United States Patent [19]

Jones

[11] Patent Number: 4,765,339
[45] Date of Patent: Aug. 23, 1988

[54] CLOSED LOOP DIALYSIS SYSTEM

[75] Inventor: Jeffrey S. Jones, Salem, Va.

[73] Assignee: Solutech, Inc., Roanoke, Va.

[21] Appl. No.: 79,296

[22] Filed: Jul. 29, 1987

Related U.S. Application Data

[62] Division of Ser. No. 870,407, Jun. 4, 1986, Pat. No. 4,726,381.

[51] Int. Cl.$^4$ .............................................. A61B 5/00
[52] U.S. Cl. .................................. 128/632; 73/863.23
[58] Field of Search ................... 128/632, 635; 604/96, 604/167; 422/101; 73/19, 863.23

[56] References Cited

U.S. PATENT DOCUMENTS

| | | | |
|---|---|---|---|
| 3,313,299 | 4/1967 | Spademan | 604/167 |
| 3,512,517 | 5/1970 | Kadish et al. | 128/632 |
| 3,572,315 | 3/1971 | Cullen | 128/632 |
| 3,640,269 | 2/1972 | Delgado . | |
| 3,640,393 | 2/1972 | Hurtig | 73/863.23 |
| 3,649,199 | 3/1972 | Littlejohn | 128/632 X |
| 3,658,053 | 4/1972 | Fergusson et al. | 128/632 |
| 3,830,106 | 8/1974 | Gardner et al. . | |
| 3,893,448 | 7/1975 | Brantigan | 128/632 |
| 3,981,297 | 9/1976 | Dunn et al. | 128/632 |
| 4,016,863 | 4/1977 | Brantigan | 128/632 |
| 4,016,864 | 4/1977 | Sielaff et al. | 128/26 |
| 4,221,567 | 9/1980 | Clark et al. | 128/635 X |
| 4,240,912 | 12/1980 | Stumpf et al. . | |
| 4,265,249 | 5/1981 | Schindler et al. | 128/635 |
| 4,267,023 | 5/1981 | Frant et al. | 204/1 T |
| 4,311,789 | 1/1982 | Nylen et al. | 435/10 |
| 4,446,106 | 5/1984 | Nelson et al. | 422/72 |
| 4,515,584 | 5/1985 | Abe et al. | 604/66 |
| 4,516,580 | 5/1985 | Polanyi | 128/635 |
| 4,576,590 | 3/1986 | Fiddian-Green | 128/632 |
| 4,694,832 | 9/1987 | Ungerstedt | 128/632 |

FOREIGN PATENT DOCUMENTS 3146644 6/1983 Fed. Rep. of Germany ...... 128/632

OTHER PUBLICATIONS

Kirk-Othmer, *Encyclopedia of Chemical Technology*, 3rd ed., vol. 7, John Wiley & Sons, N.Y. (1979), pp. 564–579.

Kirk-Othmer, *Encyclopedia of Chemical Technology*, 3rd ed., vol. 13, John Wiley & Sons, N.Y. (1981), pp. 720–734.

Kirk-Othmer, *Encyclopedia of Chemical Technology*, 3rd ed., vol. 19, John Wiley & Sons, N.Y. (1982), pp. 298–313.

Brantigan et al., "A Nonthrombogenic Diffusion Membrane . . ." *Journal of Applied Physics*, vol. 28, No. 3, Mar. 1970, pp. 375–377.

*Primary Examiner*—Lee S. Cohen
*Attorney, Agent, or Firm*—Isaksen, Lathrop, Esch, Hart & Clark

[57] ABSTRACT

An apparatus and a method of use for removing specified dialyzable components from a complex reference fluid such as, for example, blood. The invention includes a semi-permeable tubular dialysis membrane, which is inserted into the reference fluid. An equilibration fluid is injected into the tubular membrane and allowed to equilibrate with the outside reference fluid. The equilibrated fluid is then removed for analysis.

6 Claims, 3 Drawing Sheets

DEPTH OF NEEDLE

CLOSED LOOP DIALYSIS SYSTEM

This is a division of application Ser. No. 870,407, filed June 4, 1986, now U.S. Pat. No. 4,726,381.

BACKGROUND OF THE INVENTION

1. Field of the Invention

The present invention is directed to a dialysis system and more specifically to a method and apparatus for analyzing and altering the component structure of a complex reference fluid, such as blood, by use of a dialysis system. The present invention is also directed to a method and apparatus which enables the determination of the concentration of a low-molecular-weight compound in a complex fluid.

2. Discussion of the Prior Art

Several methods are known for determining the component structure of a complex fluid. For purposes of this invention a complex fluid is a fluid medium which contains a variety of components having different molecular weights. Non-limiting examples of complex fluids include blood, biological culture media such as fermentation liquids, and air. For purposes of explanation only, the present invention will be primarily directed to a blood dialysis system. However, it should be understood that the device of the present invention has far reaching potential beyond blood dialysis. Examples of other uses are specified elsewhere in this text.

One well known procedure for determining the component structure of, for example, blood is to withdraw the blood for analysis under a microscope or by other suitable means such as spectrophotometric analyzers, etc. This method is highly useful for a variety of blood tests. However, successfully withdrawing blood from a patient without insulting the integrity of the blood is a difficult procedure. For example, when exposed to the atmosphere, blood clots quickly which could alter test results. Further, any time blood is withdrawn by means of a pump system, the corpuscular components such as the red blood cells may be injured, which could alter the chemistry of the bloodstream. Further still, withdrawing blood from an infant whose blood system may total 30 to 40 milliliters (ml) blood could create a serious blood deficiency. Multiple blood withdrawals, even in minute amounts, could exsanguinate and thus traumatize the infant's system.

Separating microscopic components from fluids by dialysis is also well known to the art. Kirk-Othmer in *Encyclopedia of Chemical Technology*, Third Edition, Vol. 7, John Wiley & Sons, New York (1979) at page 564 defines dialysis as a membrane transport process in which solute molecules are exchanged between two liquid phases. The process proceeds in response to differences in chemical potentials between the liquids. There is usually little difference in pressure between the two phases. The membrane separating the liquids permits a diffusional exchange between at least some of the molecular species present while effectively preventing any convective exchange between, or comingling with, the solution. Thus, in basic principle, the two solutions will come into equilibrium, i.e., a state of balance or equality, across a semi-permeable membrane. However, large molecular structures in the fluid generally will not traverse the semi-permeable membrane and do not equilibrate across the membrane.

Dialysis has found many uses in the prior art ranging from biotechnological applications, such as blood dialysis in kidney machines, to industrial applications, i.e., fermentation fluid analysis, chemical separations and chemical analysis.

By far, the largest contemporary use of dialysis involves the treatment of blood, particularly associated with hemodialysis (Kirk-Othmer, supra at page 574). Much of the prior art involving analysis by dialysis is directed to blood analytical procedures. Examples of this procedure follow.

U.S. Pat. No. 4,016,864 to Sielaff et al is generally related to a diffusable tubular membrane in the form of a catheter which is introduced percutaneously into the bloodstream and serves as a conduit for carrier gas in blood gases. Equilibration is allowed to occur between the blood gases and the carrier gas through the membrane. The equilibrated gas is then removed from the diffusable membrane to another area for analysis by displaced volume or reduced pressure.

U.S. Pat. No. 4,156,580 to Polanyl is directed to a continuous blood gas monitoring system. The object behind this invention is to analyze components in a fluid mixture by employing diffusion of the component to be determined to a membrane. The apparatus comprises a probe, a circulating test fluid, and a gas measuring device. The probe is preferably a tube or catheter dwelling in the fluid. A portion of the distal end of this tube is covered with a thin membrane of gas permeable and blood impermeable membrane. The membrane is wound around the outside of the probe tube in spiral fashion.

U.S. Pat. No. 4,265,249 to Schindler et al is directed to an apparatus for the continuous chemical analysis of body fluids. The surface of the catheter is partially coated with a semi-permeable filter membrane. A plurality of channels are provided underneath the membrane which provide a fluid flow path for the material to be analyzed.

U.S. Pat. No. 4,311,789 to Nylen et al discloses a method for measuring the content of a low-molecular weight compound in a complex fluid, such as blood, by placing a dialyzer in contact with a complex fluid. A fraction of the fluid is passed through a semi-permeable membrane of the dialysis, contacted with a dialysis fluid and measured. The dialyzer enters the reference fluid container, such as a blood vessel, at one point and exits at another.

U.S. Pat. No. 4,221,567 to Clark et al is directed to a system for sampling and determining chemical substances in a fluid. A probe containing a liquid is inserted into a fluid matrix containing the diffusible chemical substances to be sampled and monitored. The probe is constructed of a permeable membrane. Within the probe is a tube constructed from materials such as stainless steel or glass. An opening in the tube connects the chambers of the tube and the probe. The probe containing the test fluid is placed in a fluid matrix and purportedly absorbs the chemical substances diffusing through the permeable membrane until equilibrium is reached. The equilibrated fluid is then passed through the opening in the tube and removed therefrom for analysis.

U.S. Pat. No. 3,512,517 to Kadish et al is directed to a means and apparatus for continuously monitoring blood glucose concentrations. One embodiment (FIG. 7) discloses an intravenous dialyzing catheter wherein the blood component to be measured passes through the dialyzing membrane of the catheter and is directly mixed with the analytic reagent. The blood proteins and formed elements do not pass through the dialyzing membrane and purportedly are never removed from the patient. This embodiment permits the monitoring of blood chemistry without actually removing the whole blood from the body. The catheter includes an outer dialyzing membrane and an inner tubing. The material used for the membrane is suitable for dialyzing glucose and other dialyzable blood components from the whole blood, removing the blood proteins and formed elements, i.e., white cells, red cells and platelets from the blood. A specific example is polyethylenevinylpyrrolidone, sold under the trademark PERMION-300 by Radiation Application, Inc. The dialyzed component and an enzyme reagent (for preventing coagulation) are mixed within the catheter and removed for analysis.

U.S. Pat. No. 3,572,315 to Cullen is directed to an apparatus for withdrawing gaseous constituents from a liquid for analysis of the gaseous constituents. More specifically, the invention includes a catheter which comprises a cannula having a gas permeable but liquid impervious membrane at the distal end and subatmospheric pressure means connectable with the opposite end for inducing gaseous flow from the blood stream through the cannula.

U.S. Pat. No. 3,640,269 to Delgado is directed to apparatus which is inserted in a living organism, such as the brain, which can pass fluids from or to the organism. Part of the apparatus includes a porous application bag for the displacement of fluids into or out of the sytem.

Thus, there are known several methods for determining components, specifically gas components, in the bloodstream. These methods employ reaching the equilibrium condition between a body fluid and an external fluid through a membrane followed by analytical determination of the concentration of the gas component in the external fluid. Such methods often involve the use of a hard probe-like apparatus which is often difficult to insert into the blood vessel and thus quite time consuming.

Methods for analyzing fluids by the use of dialysis in the industrial fields are also known to the art. For example, U.S. Pat. No. 4,267,023 to Frant et al is directed to measuring gases, such as sulfur dioxide, in the atmosphere by means of a chemically integrating dosimeter, composed in part of permeable membranes, which make time integrated exposures to various gases in the atmosphere.

U.S. Pat. No. 4,240,912 to Stumpf et al is directed to an immersion dialyzer specifically for measuring the content of substrates in a sterile medium.

U.S. Pat. No. 3,830,106 to Gardner et al discloses a device for use in sampling components in liquids or gaseous materials by dialysis from the liquids. A primary purpose of this device is in fermentation-type reactions.

Even with the abundance of prior art literature directed to analysis by dialysis, it has long been desirable to provide a simple, safe and efficient manner for separating a low-molecular weight compound out of a complex medium for analysis. The present invention provides such a method and apparatus.

SUMMARY OF THE INVENTION

The present invention provides a simple, safe and efficient membrane dialyzer for taking dialyzable samples from a reference fluid. The membrane dialyzer allows for the ultrafiltration of low molecular weight components from a reference fluid, such as blood, directly in the living body. Useful membranes are of the microporous type tailored to selectively remove smaller components from a reference fluid without depleting the reference fluid of other components. Thus, the integrity of the reference fluid is not significantly altered.

It is an object of the present invention to remove dialyzed or equilibrated samples from a reference fluid for analysis without the necessity of removing the reference fluid. By dialyzed or equilibrated samples is meant a solution in which solute molecules in both the reference fluid and the solution are in equal state of concentration or are in equilibrium.

It is another object of the present invention to measure at least in "real time", i.e., shortly after equilibration, various chemical constituents of a reference fluid in a manner which does not remove the reference fluid from the container.

It is also an object of the present invention to measure at least in real time various chemical constituents of a patient's blood in a fashion which does not remove the blood from the patient.

Another object of the present invention is to provide a method and apparatus for safely and efficiently injecting chemical components into a reference fluid.

These objects and others are accomplished by the present invention which is directed to a means for analyzing components in a fluid. Uses would include analyzing blood components, such as blood gases, salts, etc.; industrial uses, such as measuring pollutants in the air or other fluids; uses in the fermentation industry; and uses in the biotechnology areas, such as measuring components in a medium for growing various living organisms without having to expose the medium or the organisms to air and ever present bacteria.

The present invention is also directed to a tubular semi-permeable membrane which is closed at one end in a bag-type fashion. The membrane is substantially straight and held this way by a wire stylet. When analysis is desired, a minute amount of a dialysis or membrane solution, e.g., about 0.2 ml, is injected into the semi-permeable membrane for equilibration with the outer reference fluid. After equilibration, generally less than 5 minutes, the solution is then withdrawn and analyzed. Alternatively, the invention may operate on a continuous basis.

The preferred apparatus for removing dialyzable components from a reference fluid for analysis includes a body portion having a closed distal end. The body portion includes a tubular membrane which defines a lumen within the membrane. A stylet or stiffened rod extends along the length of the body portion in the lumen from the proximal end to the distal end for maintaining the longitudinal integrity of the body portion. An elongated tubular conduit having a lumen along its longitudinal axis is attached at one end to the proximal end of the body portion. In this manner the lumens in the body portion and the conduit communicate with each other. The conduit receives a needle or other means for injecting a dialyzable fluid to the body portion lumen.

Advantageously, this analyzer allows the monitored fluid to be analyzed in "real time" e.g., within minutes of injecting the carrier fluid, in a simple, safe and antiseptic manner without introducing a source of error by mixing non-equilibrated fluid.

DETAILED DESCRIPTION OF THE INVENTION

The basic principle of the present invention is that solutions will come into chemical equilibrium across an enclosed, tubular semi-permeable membrane. The dialysis system is placed in a fluid to be analyzed, i.e., actually within the reference fluid, and the dialysis fluid within the semi-permeable membrane, i.e., the membrane solution, is allowed to equilibrate with the reference fluid. The membrane solution is then removed for chemical analysis. Thus, the reference fluid is not disturbed and, since the membrane solution has come into equilibrium with the reference fluid, the chemical composition of the reference fluid can be determined by analyzing the membrane solution.

The enclosed, tubular semi-permeable membrane resides substantially completely in and is substantially surrounded by the reference fluid and, due to the maximized surface area of the membrane, permits the membrane solution to equilibrate in a relatively short time, on the order of 5 minutes or less. The invention can be associated with a commercially-known autoanalyzer which can periodically remove the equilibrated membrane solution and analyze it, or the membrane solution can be manually placed in the reference fluid, equilibrated, removed and analyzed at will. In other words, once the membrane solution becomes equilibrated, it can be advantageously removed at any time after equilibrium is attained.

Advantageously, the device of the present invention can analyze blood components without removing the patient's blood. The device of the present invention is placed in a blood vessel, and the membrane solution added to the enclosed tubular membrane. After equilibration with the blood, the membrane solution is withdrawn and analyzed leaving the patient's blood intact. Fresh membrane solution is then added and the cycle repeated.

A particular advantage of the present invention is that it provides a semi-permeable membrane of maximum surface area for the equilibration of specified fluid components across the membrane between the reference fluid and the membrane solution in sufficient quantity for analysis. Another advantage of the present invention is its flexibility in that the membrane solution may be withdrawn for immediate analysis without removing or even repositioning the membrane bag. Further, there is no danger in harming the reference fluid in the event the membrane bursts. This is particularly important with respect to a patient's bloodstream and specifically the bloodstream of an infant. The constituents in the membrane solution, in a sense, mimic the blood. Therefore, a burst membrane would only add constituents to the blood which are already present. This provides a great advantage over those prior art inventions which utilize a gas as the membrane solution. In such a case, a burst membrane could create a gas bubble in a blood vessel which may lead to an embolism. Further still, because only a small quantity of the membrane solution is actually inserted into the membrane bag, i.e., on the order of 0.2 ml, the solution will easily and safely dilute with the bloodstream.

Another advantage of the present invention resides in the small size of the membrane tube relative to similar devices in the prior art. The diameter of the membrane tube is designed to take up no more than about 60% of the diameter of the host blood vessel; and, because of its "floppy" or flexible membrane wall integrity, the tubular membrane system is sufficiently malleable to adjust to the flow of the bloodstream without blocking same. These and other advantages will be more thoroughly discussed in the remainder of the specification.

Not only can the device of the present invention be used to equilibrate blood components for analysis, it can also be used as a method for delivering chemicals to the bloodstream or other parts of the body, or in systems other than the body. Thus, the present invention is uniquely qualified to administer medicines in a safe, simple and efficient manner.

It should be noted that the dialysis system of the present invention is not itself a membrane solution analyzer. Rather, it collects components, to be analyzed in a membrane solution. The solution is then passed to an analysis system where the solution is analyzed.

It is within the scope of this invention to provide a continuous process for withdrawing and analyzing select components from a reference fluid and automatically adding a prescribed drug or medicament to this reference fluid based upon the aforementioned analysis. For example, the dialysis system of the present invention could be incorporated into a larger system which would serve a dual fold function of withdrawing and measuring the amount of glucose in a blood stream and automatically adding insulin, if necessary. In this manner, the entire system would act as an artificial organ. This will be further explained later in this specification.

The device of the present invention is also useful in equilibrating gaseous components in the liquid phase in the reference fluid in which it is placed. This can be done by withdrawing the equilibrated membrane solution and inserting it into any common gas analyzer.

It will be apparent to those versed in the art that the method in accordance with the present invention can of course be applied to quantitative and/or qualitative determinations of low molecular compounds in complex media other than blood, e.g., in microbiological cultivating chambers, fermentation chambers, air pollution detection devices, and others.

For example, the biotechnological and fermentation industry requires an analyzer that will analyze a medium without exposing the medium to an outside environment and contaminating the system. Analysis of an industrial solution is generally carried out by removing a sample of the solution and analyzing it by conventional means. However, any time the system is opened to the air for drawing the fluid out there is a chance of contamination. The advantage of utilizing the device of the present invention is that it can be operated in a completely enclosed environment. Therefore, no bacteria can pass in either direction through the membrane. Even if the membrane solution is contaminated outside the system, the integrity of the working medium would remain intact.

The device of the present invention can also be used in machines. For example, the fluid analyzer of the present invention can be placed in a pipeline of a machine, such as a heart/lung machine, outside a persons body, for monitoring the fluid system in the machine as desired.

DETAILED DESCRIPTION OF THE DRAWINGS

Figures 1, 2, 3:
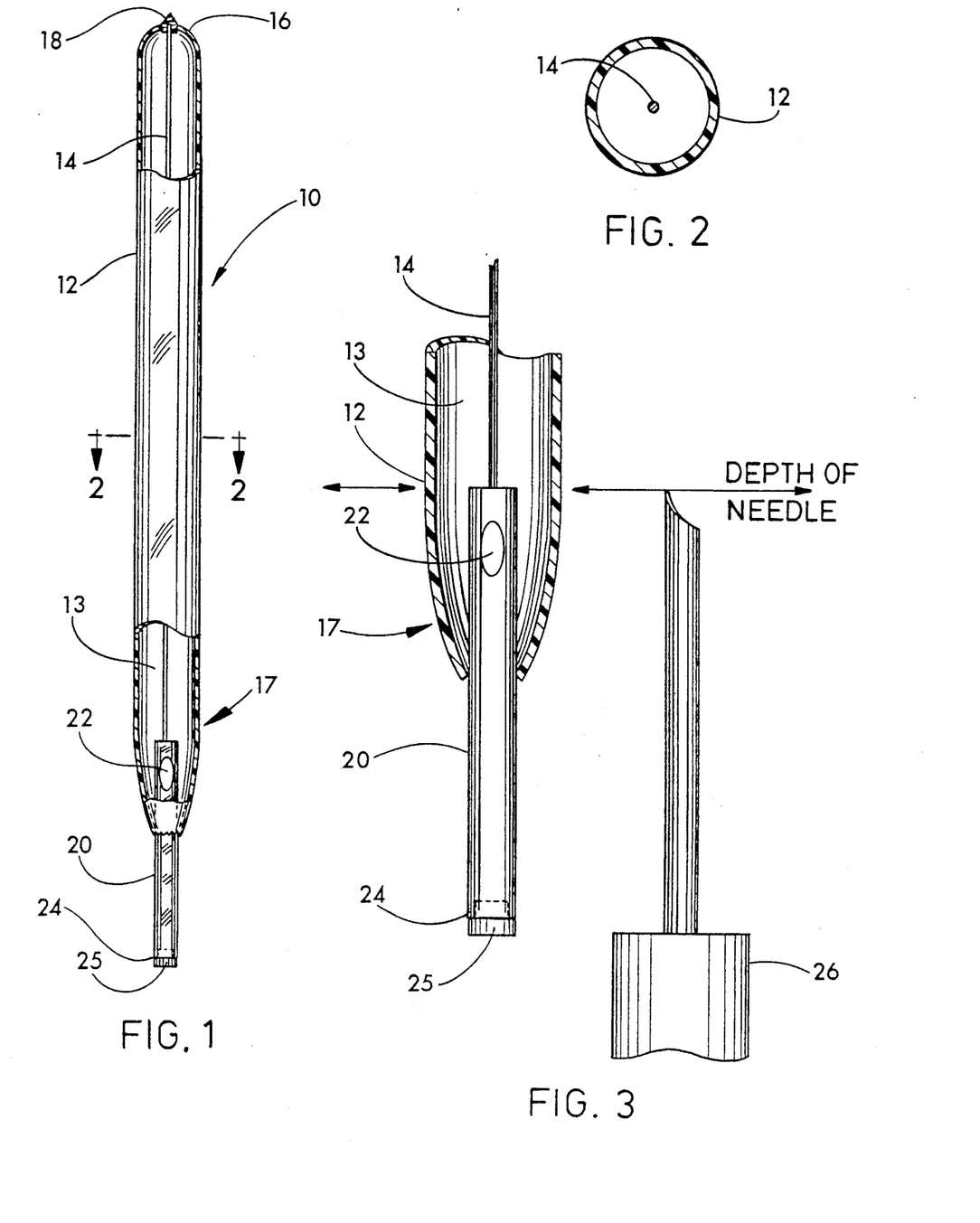
FIG. 1 is a longitudinal sectional view of a first embodiment of the dialysis system according to the present invention.
FIG. 2 is a cross-sectional view of the invention of FIG. 1 taken along lines II—II.
FIG. 3 is a partial longitudinal sectional view showing the proximal end of the invention of FIG. 1.

The present invention will now be more fully described with respect to the drawings Referring now to FIGS. 1 and 2, there is shown a dialysis system 10. In operation, dialysis system 10 is immersed in a reference fluid for equilibrating small molecular weight components between the reference fluid and the membrane solution in a batch manner. As noted previously, an example of a common reference fluid is blood within a blood vessel. System 10 includes a tubular semi-permeable membrane 12 of a flexible material described more fully hereinafter. Stylet 14, generally made of a metal, plastic or similar thin rigid wire-like material, is positioned within tubular membrane 12 and performs the dual function of maintaining the system's longitudinal integrity and giving the entire system strength for insertion into, for example, a blood vessel. Situated at the distal end 16 of system 10 is a hard generally cone-shaped tip 18 made of plastic or some other suitable material for closing off the tubular membrane and connecting stylet 14 to membrane 12. The tip of stylet 14 may be either fixedly or detachably connected to tip 18. Situated at the proximal end of system 10 is connecting tube or conduit 20 which connects tubular membrane 12 with an outside source of fluid for injection into lumen 13 of membrane 12.

An enlarged illustration of the proximal end 17 of tubular membrane 12 is found in FIG. 3. Reference is now made to FIGS. 1 and 3 for a description thereof. Situated near proximal end of conduit 20 is fluid port 22 which allows fluid communication between conduit 20 and lumen 13 of tubular membrane 12. At the distal end of conduit 20 is inlet port 24 which is designed to receive a membrane solution. Inlet port 24 may be designed to accept a Luer tip syringe (not shown). When system 10 is not in use or after the membrane solution has been inserted in lumen 13, inlet port 24 may be sealed off. The distal end of inlet port 24 may be permanently sealed with a self-sealing membrane 25. Membrane 25 allows the entry of a syringe needle, but reseals itself when the needle is withdrawn. Conduit 20 is formed of any standard tubular material known to the art. It is generally preferred that conduit 20 be made of a flexible non-permeable material, such as a plastic.

The present invention provides a method for equilibrating the components between a complex reference fluid surrounding tubular membrane 12 of system 10 and the fluid in lumen 13, i.e., the membrane solution. Of major importance to system 10 is semi-permeable tubular membrane 12 which is permeable to substances to be equilibrated for analysis and impermeable to higher molecular weight components and cellular components in the blood. Tubular membrane 12 permits the selective equilibration of materials across its wall.

The criteria for selecting a semi-permeable membrane for the purposes of the present invention are: (1) the compatability with the reference fluid must be good, so that the membrane does not contaminate the reference fluid, or cause a buildup of the reference fluid on the membrane; and (2) the permeability rate of the membrane must be great enough to allow equilibration to occur as quickly as possible. Materials such as dimethyl silicone, methyl-vinyl-polysiloxane, polycarbonate/silicone copolymers, expanded tetrafluoroethylene (Teflon—Reg. TM), and expanded polypropylene can be used. There are many other different kinds of membranes which can be used. These membranes may be tailored to perform the service desired. For example, due to the chemical makeup of a specified membrane, the membrane may be sensitive to certain drugs or poisons. The membrane would allow the drug or the poison to pass through the membrane into the membrane solution for analysis. Because proteins or other larger molecules will not traverse the semi-permeable membrane, they also cannot equilibrate across the membranes. However, the fluid in the membrane solution will actively equilibrate across the membrane, which could empty tubular membrane 12. If pressure is applied externally, the migration will cease. This process is called Colloid Osmotic Pressure. For purposes of this invention, a "colloid" is a molecule in the reference fluid which will not diffuse across the membrane. If no colloid is placed within the membrane, the water and other solutes will cross the membrane and empty the membrane. Thus, it is quite important to account for this effect. In order to speed up the equilibration process, a fluid which contains the average values of the solutes to be determined will be used. This will also include a colloid, such as for example hetastarch.

There may be very narrow limits between the high and low values of most of the measured components in a living system reference fluid. Because of this, it may be desirable to "pre-equilibrate" the membrane solution by adding specified amounts of components normally found in the reference fluid. The quantitative determination of the component structure of the membrane solution depends directly upon the component structure of the reference fluid. Generally, one would calculate the average quantity of a specified component in a reference fluid and add that amount to the membrane solution. Then, in order to determine the amount of specified component in the reference fluid, the equilibration procedure would commence from the average quantity of component in the solution rather than necessitating total equilibration of a specified component in a reference fluid from a solution of water. For example, sodium in the bloodstream is not normally present outside a certain range. Therefore, a membrane solution can have the average sodium content of what an average person would have in the blood. If an average person has 140 milliequivalents per liter (meq/l) of sodium in the blood, then 140 meq/l of sodium should be added to the membrane solution. Thus equilibration starts from the average and not from a starting point of zero. Therefore, by changing the membrane solution in the above manner, the time it takes to complete equilibrium is decreased.

The make up of the membrane solution depends upon its intended use and would be generally known to an artisan skilled in a particular field. Thus, the membrane solution by itself does not form a novel feature of the invention. Membrane solutions generally contain the average value for all components to be measured.

For blood analysis it is possible to use sterile water plus a colloid to maintain the necessary colloid osmotic pressure; but equilibration proceeds on a faster scale if the average value of the component to be measured is already incorporated into the membrane solution. A standard membrane solution for blood analysis is of the saline-type such as, for example, a 0.9% saline/bicarbonate solution.

For use in blood, a preferred membrane solution may contain the following ingredients in the following approximate proportions: about 140 meq/l sodium, 4 meq/l potassium, 110 meq/l chloride, 10 milligrams/deciliter (mg/dl) calcium, 4 mg/dl magnesium, and 90 mg/dl glucose. The membrane solution could also include a colloid as described above. This membrane solution could be used for anyone except the unusual patient with a hyperosmolar condition, i.e., very severe diabetes with a very elevated glucose level. In this unusual situation, the high osmotic pressure in bloodstream, generated as a result of the glucose level, would tend to remove fluid from the membrane. Therefore, the membrane solution should inlcude increased amounts of glucose or colloid to maintain the fluid within the membrane.

System 10 can be made in a variety of sizes depending upon the system to be monitored. For example, for a system useful in a blood vessel having an average diameter of 3 millimeters (mm), the diameter of the tubular membrane should be no more than about 2.2 mm across. This allows a 40% opening in the blood vessel which is adequate to insure safe flow of the blood in the blood vessel. The length of the tubular membrane is dependent upon its diameter. Bearing in mind that the quantity of membrane solution added to system 10 is no more than about 0.2 ml, for purposes of this example, the length should be approximately 7 cm long. For purposes of blood analysis, the diameter of system 10 ranges from 2 to 2.5 mm.

A procedure for inserting tubular membrane 12 of system 10 into a patient for blood analysis is as follows. The patient is prepared in a standard fashion for venipuncture or arterial access. There are several known methods for inserting tubes into the blood vessel of a patient. For purpose of explanation only, reference is made to a breakaway needle, such as L-Cath (Reg. TM—Luther Medical), which is percutaneously inserted into the vessel and system 10 is inserted therethrough. It is preferred to have lumen 13 of system 10 evacuated prior to insertion. The breakaway needle is then removed from the vessel and broken in half to be removed completely. System 10 is then secured to the patient at conduit 20 by adhesive tape or other known means for a common intraveneous line.

When analysis is desired, the membrane solution is injected into tubular membrane 12 through conduit 20 by means of a standard syringe 26. The diameter of conduit 20 is preferably only large enough to accommodate the needle of syringe 26. The needle of syringe 26 is inserted into sealing plug 25 of conduit 20 such that the distal end of the needle is adjacent to fluid port 22. At that point membrane solution is injected into lumen 13 of tubular membrane 12 and allowed to equilibrate. The membrane solution is then withdrawn with a similar syringe and needle, both of which are dry in order to prevent any error in analysis due to dilution. As the membrane solution is evacuated from system 10, tubular membrane 12 collapses against itself thereby further reducing the volume of system 10 in the blood vessel.

Inserting the needle of syringe 26 to where the distal end of the needle is in communication with fluid port 22 is of primary importance in order to minimize the "dead space" in conduit 20. "Dead space" is that space which will be filled with a dialyzing fluid but not analyzed. If the equilibrated membrane solution is combined with non-equilibrated solution found in conduit 20, there will be a source of error due to dilution. Because the quantity of membrane solution in system 10 can be extremely small, e.g., 0.2 ml or less, other fluid in the system which is not equilibrated will create a large source of error. Due to the structure of conduit 20 and the method of injecting and withdrawing membrane solution to and from tubular membrane 12, the source of error from fluid in the dead space is minimized. If desired, especially for tubular membranes having large diameters, a self-sealing membrane may separate the tubular membrane from the conduit. Once the solution is injected into the tubular membrane by, for example, a needle, it is withdrawn from the self-sealing membrane, which is then sealed thereby eliminating solution backflow into the conduit. The self-sealing membrane may be made of any well known self-sealing material such as, for example, rubber.

Once the equilibrated fluid has been removed from tubular membrane 12, it is analyzed by any conventional analyzer known to the art for the intended purpose. Such analyzers can be mass spectrometers, ion specific electrodes and chemical analyzers. Reference is made to U.S. Pat. No. 4,446,106 for a non-limiting example of a system analyzer.

Because of the size of system 10, equilibration is rapid, generally not more than 5 minutes. Equilibration can be as quick as a few seconds. Therefore, by use of the batch system as shown in FIGS. 1 and 2, analysis could take place approximately every 5 minutes by injecting a solution, equilibrating, withdrawing that solution for analysis and injecting a new solution.

Advantageoulsy, the device of the present invention also allows for long time interval between analysis. Once the membrane solution is injected into system 10 and allowed to equilibrate, it can remain there undisturbed for extended periods of time, i.e., up to 24 hours and beyond, before the solution is withdrawn for analysis. The process can also be automated by having an analyzer connected to the system and adapted to withdraw and replenish the membrane solution on a cyclical basis.

Figures 4, 5, 6, 7:
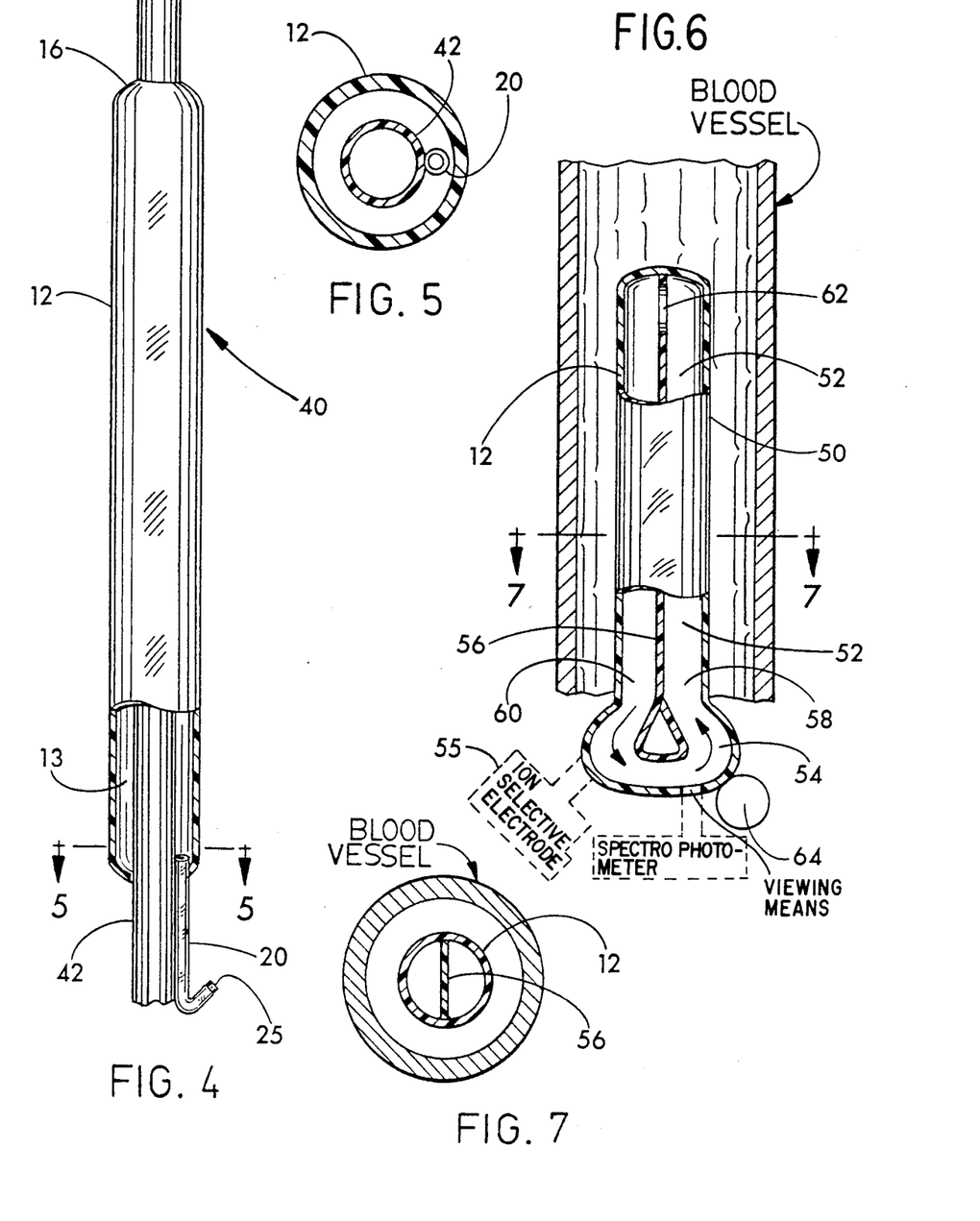
FIG. 4 is a longitudinal sectional view of a second embodiment of the dialysis system according to the present invention.
FIG. 5 is a cross-sectional view of the invention of FIG. 4 taken along lines V—V.
FIG. 6 is a longitudinal sectional view of a third embodiment of the dialysis system according to the present invention.
FIG. 7 is a cross-sectional view of the invention of FIG. 6 taken along lines VII—VII.

Reference is now made to FIGS. 4 and 5 which illustrate another embodiment of the present invention. For component parts which have parts similar to the system shown in FIGS. 1 and 2, the same reference numerals will be used. In FIGS. 4 and 5, there is shown a system 40 which includes tubular membrane 12 surrounding a standard catheter 42. Catheter 42 includes a plastic-like tube, which is well known to the art. Tubular membrane 12 is attached around a portion of catheter 42 such that catheter 42 is longitudinally directed through the central axis of tubular membrane 12. Like the system shown in FIGS. 1 and 2, conduit 20 connects tubular membrane 12 with the outside environment for injection and withdrawal of the membrane solution. Sealing plug 25, attached to conduit 20, prevents unwanted leakage from the system.

The procedure for inserting the catheter membrane combination is similar to that for a normal catheter insertion. Generally, the center of the catheter has a hollow needle running down its length and protruding from the end. Once the needle has punctured the blood vessel, the catheter line with tubular membrane 12 is slipped into the vessel and the central needle is withdrawn. The procedure for analyzing the various components in the bloodstream is similar to that described with reference to FIGS. 1 and 2.

A third channel, not illustrated, can be attached to the catheter membrane combination and communicate directly with the blood or body fluid and may be used to remove samples of the bloodstream or to introduce medicaments thereto should it not be practical to use system 40 for both analysis and medicaments introduction.

Reference is now made to FIGS. 6 and 7 for a third embodiment of the present invention. Unlike FIGS. 1-5 which illustrate a batch method of analysis, in FIGS. 6 and 7 there is shown a continuous flow analyzer 50 in which the equilibrated solution does not have to leave the system. This is a closed loop system where the fluid is continuously being equilibrated. Again, similar component parts in FIGS. 6 and 7 will have the same reference numerals as in FIGS. 1-5. Continuous system 50 comprises system equilibration area 52 and reservoir 54. Bisecting area 52 in a longitudinal fashion is septum 56 which divides the equilibration area 52. Area 52 is surrounded by tubular semi-permeable membrane 12, and reservoir 54 may be made of an impermeable membrane material. System equilibration area 52 is inserted into a blood vessel in a manner similar to that described with respect to FIGS. 1 and 2. The reservoir end 54 remains outside of the patient's body for sampling. Septum 56 in system equilibration area 52 divides the tubular portion of system equilibration area 52 into an entrance section 58 and an exit section 60. The arrows in system 50 designate the flow of the membrane solution. Entrance section 58 and exit portion 60 are connected at the distal end of system 50 by means of opening 62. The flow of the membrane solution is maintained by a pump means 64 known to the art such as, for example, a roller pump. The membrane solution may be withdrawn from reservoir 54 for analysis and replenished as needed. This can be done manually or it can be automated. It is also possible and preferable to put a clear window-type portion of tubing into the system at reservoir 54 so that an instrument, such as a spectrophotometer, could make direct measurements without removing any of the membrane fluid. Alternatively an analyzing system such as an ion selective electrode 55 can be placed directly in the flow of the membrane solution in reservoir 54 for analyzing the fluid.

Figures 8, 9, 10, 11, 12:
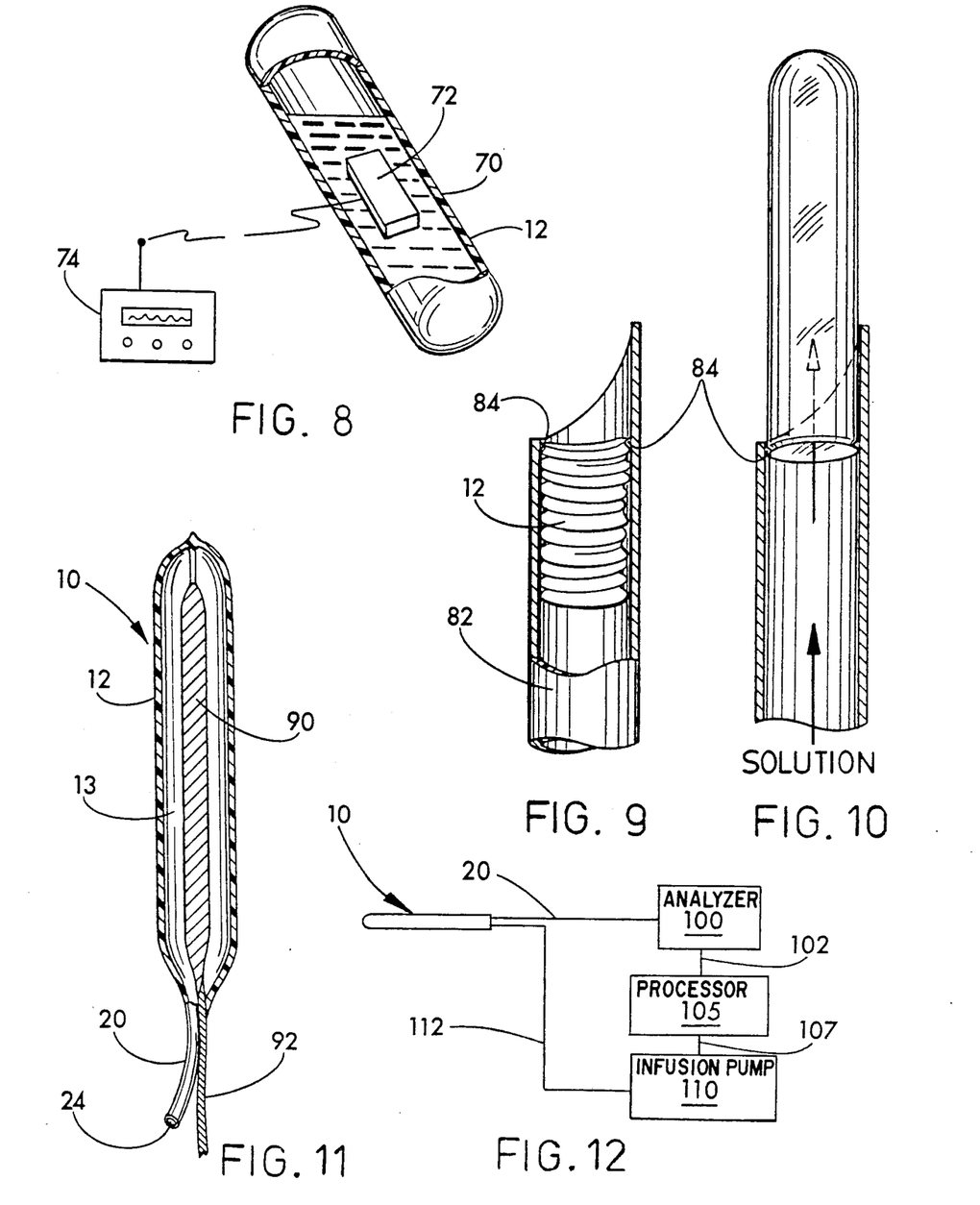
FIG. 8 is a longitudinal sectional view of a fourth embodiment of the dialysis system according to the present invention.
FIGS. 9 and 10 are longitudinal sectional views of a fifth embodiment of the dialysis system of the present invention.
FIG. 11 is a cross-sectional, longitudinal view of a sixth embodiment of the dialysis system according to the present invention.
FIG. 12 is a diagrammatic representation of a seventh embodiment of the dialysis system according to the present invention.

Reference is now made to FIG. 8 for yet another embodiment of the present invention which is directed to a detached sack or pillow 70 of membrane solution which includes a computer chip 72 for transmitting analysis information by radio waves to a radio receiver 74. Pillow 70 is swallowed by the patient, and the membrane solution contained within is equilibrated as the pillow passes through the patient's system. For example, such a system could be used to measure the gastric acidity of the patient. Due to the computer chip 72 and radio receiver 74, the information generated from the equilibrated membrane solution can be measured and analyzed by means of receiver 74.

FIGS. 9 and 10 refer to an alternative embodiment to FIGS. 1 and 5, which eliminates the need for a wire stylet. In this embodiment, tubular membrane 12 is folded inside a hollow insertion needle 82. The proximal end of membrane 12 is attached to needle 82 at junction 84 by any commonly known means for attachment. The needle is then inserted into a blood vessel. Membrane solution is then allowed to flow through the needle and, due to the pressure of the membrane solution, effectively "pops" tubular membrane 12 out of needle 82 and into the blood vessel. The membrane solution then fills tubular membrane 12 for equilibration and is analyzed according to procedures disclosed with reference to FIGS. 1 and 2.

FIG. 11 refers to another embodiment of the present invention in which analyzer probe 90 is housed within tubular membrane 12. A non-limiting example of a well known probe for use in this embodiment is an ion selective electrode. An ion selective electrode is like a pH meter for measuring hydrogen ions. Several different ion selective electrodes are made for measuring sodium, glucose, etc. Reference is made to Kirk-Othmer, *Encyclopedia of Chemicals Technology*, Third Edition (1981), Vol. 13, pp. 720-734 which is incorporated herein by reference to describe ion selective electrodes.

In this embodiment the membrane solution in lumen 13 is equilibrated in the manner described with reference to FIG. 1 and the equilibrated information is "analyzed" by probe 90. The information generated by probe 90 is delivered to a reading unit and print-out (not shown) via probe access 92. Probe access 92 is a wire which will allow information to be transmitted from the dialysis system to a reading unit which interprets the information passed on by ther analyzer. Membrane 12 and the membrane solution in lumen 13 advantageously protect probe 90 from the reference fluid environment. For example, proteins in the reference fluid may attach to the probe causing it to function erratically. The membrane keeps the proteins away from the probe allowing for accurate measurements.

The range of blood components which could be measured by the devices disclosed herein is limited only by the permeability of the membrane and by the sample size required by the analyzer used. The size of the previously described system, particularly the volume of the membrane solution, depends upon the volume requirement of the analyzer. It could be anticipated that as analyzers are able to analyze smaller samples that the devices could also be scaled down. It would also be anticipated that the devices would come in several sizes and with membranes of different permeability depending upon their intended uses.

The invention described herein has several distinct advantages over similar prior art apparata. First, the dialysis system facilitates analysis with minimum error from "dead space" dilution. Further, and most importantly with respect to disease prevention, the reference fluid is not disturbed. Therefore, one can measure components of blood without handling the blood, thereby effectively eliminating the risk of disease transmission. The method and apparatus of the present invention also has a failsafe mechanism in that only a minute amount of liquid is actually equilibrated for analysis. The constituents in the liquid are similar to the reference fluid so that if the tubular membrane should burst, only a small amount of fluid which virtually mimics the reference fluid, would enter the system. Further still, due to the small size of the present invention and the flexibility of the membrane structure, there is no worry that a blood vessel would become blocked by use of the system.

The device of the present invention has practically unlimited potential. For example, it is not unlikely to think that this device will be implanted into a patient upon admission into the hospital for routine blood work testing. Because the invention can remain in patient for an extended period of time, there is no need to remove it after every testing. All that is required is to inject a membrane solution and allow the solution to equilibrate. Additionally, the device of the present invention could be attached to a portable monitor and administration system for simultaneously monitoring the blood system and administering medicaments as necessary. For example, this has useful application for diabetes patients who require systematic doses of insulin. Used in this capacity, the entire system operates like an artificial organ.

Reference is now made to FIG. 12 for a diagrammatic illustration of one type of artificial organ. By artificial organ is meant a synthetic or "man-made" device which is capable of replacing or assisting the natural organ's function in a manner similar to the natural method. A representative example of an artificial organ is disclosed in U.S. Pat. No. 4,515,584. A further definition and description of artificial organs can be found in Kirk-Othmer, *Encyclopedia of Chemical Technology*, Third Edition, Vol. 19 (1982), pages 298–313, which is incorporated herein by reference. Referring now to FIG. 12, dialysis system 10 is inserted into a body organ or blood vessel in a manner similar to that described with reference to FIG. 1. The targeted reference fluid or blood components are then passed through membrane 12 into lumen 13 during equilibration. After the membrane solution in lumen 13 has become fully equilibrated, it is forwarded via connecting tube 20 to analyzer 100 for analysis. A description of suitable analyzers for use in this embodiment may be found elsewhere in the specification. The membrane solution may be removed by a syringe as described with reference to FIGS. 1–3, or the solution may be forwarded directly to analyzer 100 on a continuous basis with the aid of, for example, a roller pump. Analyzer 100 analyzes the component content of the membrane solution and directs the information obtained from the analysis via access 102 to processor 105 which calculates whether a specific deficiency is occurring in the blood stream. Processor 105 may be a programmable computer known to the art. The information generated from processor 105 is fed via access 107 to infusion pump 110 which delivers controlled amounts of an injection dose of a nutrient or medicine, in accordance with the information supplied by processor 105 to the blood stream via access 112. The modification of the blood stream is under the control of a specified program in processor 105. It is within the scope of the invention to deliver the make-up components directly to the blood stream or via the membrane solution. The augmented solution is transferred to the same dialysis system 10 which allows the make-up components to diffuse out of system 10 into the blood stream. This completes the cycle. Thus, the artificial organ as described generates a means for reviewing a chemical or a nutrient in a blood system, e.g., insulin release.

Further still, the system of the present invention has utility in areas other than blood analysis. The device can be easily adapted to measure various gases and pollutants in air and water, for example, in an industrial environment.

Other uses include the measurement of components in a liquid of an industrial process, such as a fermentaion broth. Still other uses for the system of the present invention are found in measuring the component makeup of culture media in the biotechnological areas.

Although the present invention has been described with preferred embodiments, it is to be understood that modifications and variations may be resorted to, without departing from the spirit and scope of this invention, as those skilled in the art will readily understand.

What is claimed is:

1. A continuous closed-loop apparatus for equilibrating specified dialyzable components in a complex fluid for analysis comprising:
    (1) a body portion including an elongated semipermeable tubular dialyzing membrane having a proximal end and a distal end, said body portion being separated into a first and second passageway by a dividing means extending the length of said body portion, said first and second passageways communicating with each other by means of an opening in said dividing means near said distal end of said elongated tubular membrane;
    (2) a looped reservoir portion comprising a nondialyzable tubular membrane, said membrane having a first end and a second end, said first end being in direct communication with said first body portion passageway and said second end of said reservoir portion being in direct communication with said second body portion passageway thereby effecting a continuous closed loop passageway;
    (3) membrane solution within said continuous closed loop passageway for receiving said specified dialyzable components from said complex fluid by equilibration;
    (4) means for effecting membrane solution flow in a defined direction within said apparatus such that said membrane solution receives said specified dialyzable components in said body portion; and
    (5) means associated with said reservoir portion for analyzing said dialyzable components.

2. The apparatus according to claim 1, wherein said dialyzing membrane is gas permeable.

3. The apparatus according to claim 1, wherein said tubular dialyzing membrane is selected from the group consisting of cellulose, dimethyl silicone, methyl-vinyl-polysiloxane, polycarbonate/silicone copolymers, expanded tetrafluoroethylene and expanded polypropylene.

4. The apparatus according to claim 1, wherein said apparatus is constructed for insertion percutaneously into a blood vessel in a direction extending along the principal axis thereof.

5. The apparatus according to claim 4, wherein said blood vessel is approximately 3 mm in diameter and said body portion is approximately 2.2 mm in diameter, allowing a 40% opening in the blood vessel.

6. The apparatus according to claim 1 further comprising a viewing means attached to said reservoir portion, wherein said means for analyzing is a spectrophotometer which analyzes dialyzable components by said viewing means attached to said reservoir portion.

* * * * *